(12) United States Patent
Isaacs et al.

(10) Patent No.: US 10,864,148 B2
(45) Date of Patent: Dec. 15, 2020

(54) COMPOSITIONS AND METHODS FOR STABILIZATION OF RETINOIDS

(71) Applicant: Pangaea Laboratories Limited, Elstree (GB)

(72) Inventors: Daniel Isaacs, Elstree (GB); Elliot Isaacs, Elstree (GB); Kavitha Murugesan, Elstree (GB)

(73) Assignee: Pangaea Laboratories Ltd., Elstree (GB)

(*) Notice: Subject to any disclaimer, the term of this patent is extended or adjusted under 35 U.S.C. 154(b) by 0 days.

(21) Appl. No.: 16/378,427

(22) Filed: Apr. 8, 2019

(65) Prior Publication Data

US 2019/0307662 A1 Oct. 10, 2019

(30) Foreign Application Priority Data

Apr. 6, 2018 (GB) .................................. 1805798.4

(51) Int. Cl.
| | | |
|---|---|---|
| *A61K 8/31* | (2006.01) | |
| *A61Q 19/08* | (2006.01) | |
| *A61K 8/84* | (2006.01) | |
| *A61K 8/06* | (2006.01) | |
| *A61K 8/67* | (2006.01) | |
| *A61K 8/11* | (2006.01) | |
| *A61K 8/73* | (2006.01) | |
| *A61K 8/9789* | (2017.01) | |

(52) U.S. Cl.
CPC .................. *A61K 8/31* (2013.01); *A61K 8/06* (2013.01); *A61K 8/11* (2013.01); *A61K 8/671* (2013.01); *A61K 8/738* (2013.01); *A61K 8/84* (2013.01); *A61K 8/9789* (2017.08); *A61Q 19/08* (2013.01)

(58) Field of Classification Search
CPC ... A61K 8/31; A61K 8/84; A61K 8/06; A61K 8/671; A61K 8/11; A61K 8/738; A61K 8/9789; A61K 19/08
See application file for complete search history.

(56) References Cited

U.S. PATENT DOCUMENTS

| | | | | |
|---|---|---|---|---|
| 2003/0165545 A1* | 9/2003 | Huth | ................... | A61K 9/0048 424/400 |
| 2003/0165546 A1 | 9/2003 | Resch et al. | | |
| 2012/0305415 A1* | 12/2012 | Gleyzer | ................ | A45D 34/00 206/220 |

FOREIGN PATENT DOCUMENTS

| | | |
|---|---|---|
| CN | 106221703 | 12/2016 |
| CN | 106380340 | 2/2017 |
| CN | 106748262 | 5/2017 |
| CN | 107021832 | 8/2017 |
| CN | 107188653 | 9/2017 |
| CN | 107151180 | 9/2019 |
| DE | 102005004187 | 8/2006 |
| JP | 2005330257 | 12/2005 |
| KR | 20090113614 | 11/2009 |

OTHER PUBLICATIONS

UK IPO, Search Report in child UK application GB1904056.7, dated Aug. 1, 2019.
UK IPO, Combined Search and Examination Report in corresponding UK application GB1805798.4, dated Nov. 1, 2018.
Specialchem, "Sodium Polyaspartate," cosmetics.specialchem.com/inci/sodium-polyaspartate (accessed Apr. 4, 2020).
Cosmetic Analysis, "Sodium Polyaspartate," cosmeticanalysis.com/cosmetic-ingredients/sodium-polyaspartate.html (accessed Apr. 4, 2020).

* cited by examiner

*Primary Examiner* — Ali Soroush
(74) *Attorney, Agent, or Firm* — Ryan Alley IP

(57) ABSTRACT

The present invention relates to a composition and method for stabilisation of compounds including retinoids using the synergistic effects of beta-carotene and sodium polyaspartate.

19 Claims, 5 Drawing Sheets

Example 1: Retinaldehyde with carrot seed oil - photo-degradation

| | A1 | B1 | C1 | D1 | E1 | F1 | G1 | H1 |
|---|---|---|---|---|---|---|---|---|
| Aqueous phase | | | | | | | | |
| Water | QS 100 | QS 100 | QS 100 | QS 100 | QS 100 | QS 100 | QS 100 | QS 100 |
| Glycerin | 2 | 2 | 2 | 2 | 2 | 2 | 2 | 2 |
| Oil phase | | | | | | | | |
| Caprylic/Capric Triglycerides | 6 | 6 | 6 | 6 | 6 | 6 | 6 | 6 |
| Sorbitan Olivate | 1.5 | 1.5 | 1.5 | 1.5 | 1.5 | 1.5 | 1.5 | 1.5 |
| Cetearyl Olivate | 1 | 1 | 1 | 1 | 1 | 1 | 1 | 1 |
| Thickening | | | | | | | | |
| Acryloyldimethyl Taurate | 2 | 2 | 2 | 2 | 2 | 2 | 2 | 2 |
| Active and stabilisers | | | | | | | | |
| Carrot Seed Oil | -- | -- | 2.5 | 2.5 | 2 | 1.5 | 0.5 | 0.25 |
| Sodium Polyaspartate | -- | 0.2 | -- | 0.025 | 0.05 | 0.1 | 0.15 | 0.175 |
| Retinaldehyde | 0.1 | 0.1 | 0.1 | 0.1 | 0.1 | 0.1 | 0.1 | 0.1 |
| Preservatives | | | | | | | | |
| Phenoxyethanol | 0.9 | 0.9 | 0.9 | 0.9 | 0.9 | 0.9 | 0.9 | 0.9 |

Table 1

Figure 1

| Example 2: Retinaldehyde with carrot seed oil - thermal degradation | | | | | | | | | |
|---|---|---|---|---|---|---|---|---|---|
| | A2 | B2 | C2 | D2 | E2 | F2 | G2 | H2 |
| Aqueous phase | | | | | | | | |
| Water | QS 100 | QS 100 | QS 100 | QS 100 | QS 100 | QS 100 | QS 100 | QS 100 |
| Polyacrylate Crosspolymer | 1 | 1 | 1 | 1 | 1 | 1 | 1 | 1 |
| Active and stabilisers | | | | | | | | |
| Carrot Seed Oil | -- | -- | 2.5 | 2.5 | 2 | 1.5 | 0.5 | 0.25 |
| Sodium Polyaspartate | -- | 0.2 | -- | 0.025 | 0.05 | 0.1 | 0.15 | 0.175 |
| Retinaldehyde | 0.1 | 0.1 | 0.1 | 0.1 | 0.1 | 0.1 | 0.1 | 0.1 |
| Preservatives | | | | | | | | |
| Phenoxyethanol | 0.9 | 0.9 | 0.9 | 0.9 | 0.9 | 0.9 | 0.9 | 0.9 |
| Buffering | | | | | | | | |
| Sodium Hydroxide | QS to neutralise the formulation | | | | | | | |

Table 3

Figure 2

| Example 3: Encapsulated retinaldehyde with carrot seed oil - thermal and photo-degradation | A3 | B3 |
|---|---|---|
| Aqueous phase | | |
| Water | QS 100 | QS 100 |
| Polyacrylate Crosspolymer | 1 | 1 |
| Active and stabilisers | | |
| Carrot Seed Oil | | 2 |
| Sodium Polyaspartate | | 0.05 |
| Retinaldehyde in cyclodextrin | 0.1 (RAL) | 0.1 (RAL) |
| Preservatives | | |
| Phenoxyethanol | 0.9 | 0.9 |
| Buffering | | |
| Sodium Hydroxide | QS to neutralise the formulation | |

Table 5

Figure 3

| Example 4: Retinaldehyde with pure beta-carotene – photo-degradation | A4 | B4 | C4 | D4 | E4 | F4 | G4 | H4 |
|---|---|---|---|---|---|---|---|---|
| Aqueous phase | | | | | | | | |
| Water | QS 100 | QS 100 | QS 100 | QS 100 | QS 100 | QS 100 | QS 100 | QS 100 |
| Polyacrylate Crosspolymer | 1 | | | 1 | 1 | 1 | 1 | 1 |
| Active and stabilisers | | | | | | | | |
| beta-Carotene (1%) in Ethanol | -- | -- | 2.5 | 2.5 | 2 | 1.5 | 0.5 | 0.25 |
| Sodium Polyaspartate | -- | 0.2 | -- | 0.025 | 0.05 | 0.1 | 0.15 | 0.175 |
| Retinaldehyde | 0.1 | 0.1 | 0.1 | 0.1 | 0.1 | 0.1 | 0.1 | 0.1 |
| Preservatives | | | | | | | | |
| Phenoxyethanol | 0.9 | 0.9 | 0.9 | 0.9 | 0.9 | 0.9 | 0.9 | 0.9 |
| Buffering | | | | | | | | |
| Sodium Hydroxide | QS to neutralise the formulation | | | | | | | |

Table 7

Figure 4

| Example 5: Retinaldehyde with carrot root extract – photo-degradation | A5 | B5 | C5 | D5 | E5 | F5 | G5 | H5 |
|---|---|---|---|---|---|---|---|---|
| Aqueous phase | | | | | | | | |
| Water | QS 100 | QS 100 | QS 100 | QS 100 | QS 100 | QS 100 | QS 100 | QS 100 |
| Glycerin | 2 | 2 | 2 | 2 | 2 | 2 | 2 | 2 |
| Oil phase | | | | | | | | |
| Caprylic/Capric Triglycerides | 6 | 6 | 6 | 6 | 6 | 6 | 6 | 6 |
| Sorbitan Olivate | 1.5 | 1.5 | 1.5 | 1.5 | 1.5 | 1.5 | 1.5 | 1.5 |
| Cetearyl Olivate | 1 | 1 | 1 | 1 | 1 | 1 | 1 | 1 |
| Thickening | | | | | | | | |
| Sodium Acrylate/Sodium Acryloyldimethyl Taurate Copolymer | 2 | 2 | 2 | 2 | 2 | 2 | 2 | 2 |
| Active and stabilisers | | | | | | | | |
| Carrot Root Extract | — | — | — | 5 | 5 | 4 | 3 | 1 |
| Sodium Polyaspartate | — | 0.4 | — | 0.05 | 0.1 | 0.1 | 0.2 | 0.3 | 0.35 |
| Retinaldehyde | 0.1 | 0.1 | 0.1 | 0.1 | 0.1 | 0.1 | 0.1 | 0.1 |
| Preservatives | | | | | | | | |
| Phenoxyethanol | 0.9 | 0.9 | 0.9 | 0.9 | 0.9 | 0.9 | 0.9 | 0.9 |

Table 9

Figure 5

COMPOSITIONS AND METHODS FOR STABILIZATION OF RETINOIDS

This application claims priority under 35 U.S.C. § 119 to UK Application GB1805798.4, filed Apr. 6, 2018. This UK Application is incorporated by reference herein in its entirety.

BACKGROUND

Field

The present disclosure relates to a composition for the stabilisation of retinoids, such as retinaldehyde, and a method of stabilisation thereof.

Ageing is considered to occur in two forms; intrinsic and extrinsic. Intrinsic ageing is a result of genetically determined factors over which people have no control. For example, after the age of 20 years old, on average, people produce one percent less collagen in the skin each year; collagen is important in skin elasticity. Extrinsic ageing occurs due to environmental factors such as UV radiation. People have a strong urge to stop the ageing process. However, as the skin loses its elasticity wrinkles appear. Accordingly, people who wish to prevent the ageing process often try to prevent wrinkle formation or reduce the appearance thereof.

Retinoic acid, which is a metabolite of vitamin A (retinol), is considered to be a useful compound in the prevention and treatment of wrinkles because it used by the body to produce collagen. However, retinoic acid can cause burning or scaling of the skin and/or dermatitis. It is also very susceptible to photo-degradation and, therefore, it has been recommended that it is only used at night and a strong UV protector is applied the next day. Due to these side effects, retinoic acid is only available in many countries as a prescription drug for conditions such as acne.

As a result of the problems with the application of retinoic acid to the skin cosmetic manufacturers have looked for compounds which are metabolised within the body to retinoic acid. Retinaldehyde is considered to be a good choice in anti-ageing skin creams because studies suggest that in the body it is converted to retinoic acid and retinyl esters which are a storage form of retinol. However, retinaldehyde, as with other retinoids, such as retinol, is also highly susceptible to photo and thermal damage.

Various forms of stabilisation of retinaldehyde are currently used. For example, butylhydroxytoluene (BHT) and butylhydroxyanisole (BHA), superoxide dismutase and Coenzyme Q10 are commonly used as stabilisers. However, they only offer partial protection from thermal degradation and minimal, if any, protection from photo-degradation. Accordingly, such products have a short shelf-life and have to be packaged in opaque or highly protective packaging.

Encapsulation methods have also been used to try to stabilise, retinoids such as, retinaldehyde. Cyclodextrin encapsulation, in particular, decreases thermal-damage to the retinaldehyde, however, photo-damage can still occur.

SUMMARY

An object of the present invention is to provide a composition which reduces thermal-damage and/or photo-damage of retinoids, such as, retinaldehyde.

A further object of the present invention is to provide a method of stabilising retinoids, such as, retinaldehyde.

In a first aspect of the present invention there is provided a cosmetic composition comprising beta-carotene and sodium polyaspartate.

In a second aspect of the present invention there is provided a stabilising composition comprising beta-carotene, sodium polyaspartate and retinaldehyde wherein the beta-carotene and sodium polyaspartate stabilise the retinaldehyde.

Unexpectedly the inventors have found that beta-carotene and sodium polyaspartate have a synergistic effect in the stabilisation of compositions, and, in particular, compositions which contain, retinoids, such as retinaldehyde. This unexpected synergistic effect results in a longer shelf-life for any active compound in the composition and the reduction in photo-damage reduces the need for opaque or highly protective packaging which can be unsightly, impractical and/or expensive. An additional benefit of the present composition is that as encapsulation of the active compound, such as retinaldehyde is optional, the viscosity of the composition can be the choice of the user, formulator or manufacturer as there is no need for the thick viscosity required for uniform distribution of encapsulated active compound.

Conveniently, the beta-carotene is selected from synthetic beta-carotene, isolated beta-carotene or a plant extract containing beta-carotene. Pure beta-carotene can be in the form of isolated beta-carotene or synthetic beta-carotene. The use of synthetic or isolated beta-carotene ensures that there is less risk of variable results due to, for example, unknown concentrations of beta-carotene in plant extracts of low quality. However, plant extracts are often easier to incorporate into formulations and can introduce other beneficial compounds such as vitamins and minerals to the composition.

In an embodiment of the present invention, the ratio of synthetic beta-carotene or isolated beta-carotene to sodium polyaspartate is about 1:0.1 to about 1:10. Conveniently, the ratio of synthetic beta-carotene or isolated beta-carotene to sodium polyaspartate is about 1:0.5 to about 1:5. At these ratios, chemical compounds such as retinoids, for example retinaldehyde, have reduced thermal-damage and/or photo-damage.

In an embodiment of the present invention the plant extract can be from any suitable yellow, orange or green-leafy, fruit and vegetable. The following is a non-exhaustive list of examples carrot, raspberry, palm extract, broccoli, tomato, pumpkin, squash, sweet potato, spinach, lettuce, kale, turnip greens, beet greens, cabbage, melons (in particular cantaloupe), plums, chilli powder, grapefruit, dandelion leaves, apricots, onions and/or peas.

In an embodiment of the present invention, the plant extract is from carrot. Conveniently, the carrot extract is either carrot root extract or carrot seed oil extract. It has been found that these forms of carrot extract have an advantageous synergistic effect when stabilising compositions.

In an embodiment of the present invention, the ratio of carrot extract to sodium polyaspartate is about 100:1 to about 10:1. Conveniently the ratio of carrot extract to sodium polyaspartate is about 40:1 to about 15:1. At these ratios, chemical compounds such as retinoids, an example of which is retinaldehyde, have reduced thermal-damage and/or photo-damage.

In an embodiment of the present invention, the composition further comprises retinaldehyde.

Conveniently, the concentration of retinaldehyde is up to about 0.1% weight, wherein the weight percentage is based on total composition weight. Alternatively, the concentration of retinaldehyde is about 0.05 to about 0.1%, wherein the weight percentage is based on total composition weight.

In an embodiment of the present invention, the retinaldehyde is encapsulated. Encapsulation of retinaldehyde improves the stability thereof. Conveniently, the retinaldehyde is encapsulated with cyclodextrin.

In an embodiment of the present invention, the composition of the present invention comprises at least one of a thickener, a humectant, an emulsifier, an emollient, a buffering agent and/or a preservative.

Conveniently, the thickener is present at about 0.05 to about 3% weight to weight of the final composition. In an embodiment of the present invention, the thickener is any cosmetically acceptable thickener. Conveniently, the thickener is selected from polyacrylamide cross polymer or gums. An example of the thickener used in the present invention can be selected from cross linked polyacrylate materials available under the trademark Carbopol® from Lubrizol, Xanthan gum, carrageenan, gelatin and/or pectin.

Conveniently, the humectant is present at about 0.05 to about 10% weight to weight of the final composition. In an embodiment of the present invention, the humectant is any cosmetically acceptable humectant. An example of the humectant used in the present invention can selected from glycerin, sodium PCA, hydroxy ethyl urea, sodium hyaluronate, polyhydric alcohols.

Conveniently, the emulsifier is present at about 0.5 to about 5% weight to weight of the final composition. In an embodiment of the present invention, the emulsifier is any cosmetically acceptable emulsifier. An example of the emulsifier used in the present invention can selected from non-ionic surfactants, polymeric emulsifiers, sorbitan olivate and/or cetearyl olivate.

Conveniently, the emollient is present at about 0.5 to about 15% weight to weight of the final composition. In an embodiment of the present invention, the emollient is any cosmetically acceptable emollient. An example of the emollient used in the present invention can selected from hydrocarbon oils, fatty esters, silicone oils and mixtures. Preferably, the emollient is selected from a caprylic/capric triglyceride.

Conveniently, the buffering agent is present at about 0.01 to about 1% weight to weight of the final composition. In an embodiment of the present invention, the buffering agent can be any cosmetically acceptable buffering agent. An example of the buffering agent used in the present invention can selected from sodium hydroxide or triethanolamine.

Conveniently, the preservative is present at about 0.5 to about 5% weight to weight of the final composition. In an embodiment of the present invention, the preservative can be any cosmetically acceptable preservative. An example of the preservative used in the present invention can selected from phenoxyethanol, ethylhexylglycerin, ester-derived preservatives, ethers and/or thiazoles.

The thickener, the humectant, the emulsifier, the emollient, the buffering agent and/or the preservative and the percentages thereof are chosen in order that they do not interfere with the stabilisation of the active compound in the present invention, for example, a retinoid, and in particular, retinaldehyde.

According to a further aspect of the invention there is provided a method of stabilising retinaldehyde, the method comprising providing a composition according to the present invention.

According to another aspect of the invention there is provided use of the composition according to the present invention for stabilising retinaldehyde.

The compositions of the present invention, the methods of the present invention and the use of the composition of the present invention result in a stable form of an active compound such as retinoids, and, in particular, retinaldehyde. The stabilisation allows the active compound to have a longer shelf-life, and/or reduces the need for opaque or highly protective packaging which can be expensive, impractical and unsightly. In addition, encapsulation of the active compound can be optional which allows the user of the method to choose the viscosity of the composition of the present invention. In this connection, some users of the composition prefer to apply less viscous lotions, liquids, creams or gels.

The compositions of the present invention can include a mixture of any suitable retinoids.

BRIEF DESCRIPTION OF THE DRAWINGS

Embodiments of the present invention will now be described by way of example and with reference to FIGS. 1 to 5.

FIG. 1 shows Table 1 having the ratios of the components of the emulsion compositions used in Example 1.

FIG. 2 shows Table 3 having the ratios of the components of the gel compositions used in Example 2.

FIG. 3 shows Table 5 having he ratios of the components of the gel compositions used in Example 3.

FIG. 4 shows Table 7 having the ratios of the components of the gel compositions used in Example 4.

FIG. 5 shows Table 9 having the ratios of the components of the emulsion compositions used in Example 5.

DETAILED DESCRIPTION

Example 1: —Retinaldehyde with Carrot Seed Oil—Photo-Degradation

Preparation of Test Samples:

A cosmetically acceptable emulsion composition was prepared through emulsification by combining oil phase and aqueous phase components. The composition viscosity was adjusted using a thickener. The compositions in Table 1 were utilised in the present Example. The carrot seed oil was sourced from Nepal.

Test Protocol:

Each composition was exposed to UV-radiation according to common UV weathering test conditions (UV range 200 nm to 400 nm) in a UV-chamber by leaving the test sample in a watch glass facing the UV radiation for 48 hours to simulate the effects of sunlight over a prolonged period of time. Retinaldehyde imparts a distinctive yellow colour to the composition. As retinaldehyde photo-degrades, the composition changes colour in a manner of fading/loss of yellow colour. The colour of the composition is indicative of the degree of degradation of retinaldehyde in the composition. A 20-point colour scale was used to compare the colour of each of the compositions in order to determine the extent of degradation of the composition over time when exposed to UV radiation. The colour scale ranged from deep yellow (labelled 20) which was indicative of a stable composition to off-white (labelled 1) which was indicative of a completely degraded composition. Colour scores were taken using visual analysis of three evaluators, with the final score being the average of the three.

After 48 hrs, the colour of the composition was compared to the colour of the control a freshly prepared composition with deep yellow colour due to the non-degraded retinaldehyde. The colour score for each composition is shown in Table 2.

The synergy column represents the improvement to stabilising retinaldehyde compositions, relative to the sum of the improvements from individual stabilisers. For example, if the individual colour score of a sample stabilised by carrot seed oil alone was 9, and by sodium polyaspartate alone was 2, and the score for a certain combination of the two was 18, the synergy level is +7.

TABLE 2

UV Test
Composition becomes lighter as it is degraded by UV light
Colour Scale:
Deep Yellow: 20 (starting colour)
Off-white: 1 (fully degraded)

| Samples | Ratios CSO:SPA:RAL | Colour Score at the end point | Synergy of CSO + SPA |
|---|---|---|---|
| A1 | 0:0:1 | 1 (fully degraded) | N/A |
| B1 | 0:2:1 | 4 (very slightly stabilised) | N/A |
| C1 | 25:0:1 | 9 (partially stabilised) | N/A |
| D1 | 25:0.25:1 | 15 | 2 |
| E1 | 20:0.5:1 | 17 (stabilised) | 3 |
| F1 | 15:1:1 | 17 (stabilised) | 3 |
| G1 | 5:1.5:1 | 13 | 0 |
| H1 | 2.5:1.75:1 | 11 | −2 |

Example 2: —Retinaldehyde with Carrot Seed Oil—Thermal Degradation

Preparation of Test Samples

A cosmetically acceptable gel composition was prepared through a cold process gelling method by dispersing the thickener in solution and then neutralising by adding a buffering agent as required. The compositions in Table 3 were utilised in the present Example. The carrot seed oil was sourced from Nepal.

Test Protocol

Each composition was exposed to heat by leaving the test sample in a temperature-controlled oven at 45° C. for 7 days to simulate the effects of thermal oxidation over prolonged periods. Retinaldehyde imparts a distinctive yellow colour to the composition. As retinaldehyde degrades with heat, the composition changes colour from yellow to reddish brown which is converse to photo-degradation. A change in colour of the composition, towards reddish brown is, therefore, indicative of the degree of thermal degradation of retinaldehyde in the composition. A 20-point colour scale was used to compare the colour of each of the compositions in order to determine the extent of degradation of the composition over time when exposed to heat. The colour scale ranged from deep yellow (labelled 1) which was indicative of a stable composition to reddish brown (labelled 20) which was indicative of a completely degraded composition.

After 7 days the colour of the composition was compared to the colour of the control a freshly prepared composition with deep yellow colour due to the non-degraded retinaldehyde. The colour score for each composition is shown in Table 4.

The synergy column represents the improvement to stabilising retinaldehyde compositions, relative to the sum of the improvements from individual stabilisers. For example, if the individual colour score of a sample stabilised by carrot seed oil alone was 9, and by sodium polyaspartate alone was 2, and the score for a certain combination of the two was 18, the synergy level is +7.

TABLE 4

Heat Test
Composition becomes darker as it is degraded by heat
Colour Scale:
Deep Yellow: 1 (starting colour)
Reddish-brown: 20 (fully degraded)

| Samples | Ratios CSO:SPA:RAL | Colour Score at the end point | Synergy of CSO + SPA |
|---|---|---|---|
| A2 | 0:0:1 | 20 (fully degraded) | N/A |
| B2 | 0:2:1 | 18 (very slightly stabilised) | N/A |
| C2 | 25:0:1 | 9 (partially stabilised) | N/A |
| D2 | 25:0.25:1 | 3 (stabilised) | 6 |
| E2 | 20:0.5:1 | 3 (stabilised) | 6 |
| F2 | 14:1:1 | 3 (stabilised) | 6 |
| G2 | 5:1.5:1 | 8 (partially stabilised) | 1 |
| H2 | 2.5:1.75:1 | 15 | −2 |

Example 3: —Encapsulated Retinaldehyde with Carrot Seed Oil—Thermal and Photo-Degradation A cosmetically acceptable gel composition was prepared through cold process gelling method using cyclodextrin encapsulated retinaldehyde. The compositions in Table 5 were utilised in the present Example. The carrot seed oil was sourced from Nepal.

Test Protocol:

Samples of A3 and B3 were subjected to either heat or light induced degradation as per the protocols below. The results for each condition were captured and then consolidated to compare the degree of stabilisation imparted by the combination of CSO and SPA.

Heat Test:

Each composition was exposed to heat by leaving the test sample in a temperature-controlled oven at 45° C. for 7 days to simulate the effects of thermal oxidation over prolonged periods. Retinaldehyde imparts a distinctive yellow colour to the composition. As retinaldehyde degrades with heat, the composition changes colour from yellow to reddish brown. The colour of the composition therefore be indicative of the degree of degradation of retinaldehyde in the composition. A 20-point colour scale was used to compare the colour of each of the compositions in order to determine the extent of degradation of the composition over time when exposed to heat. The colour scale ranged from deep yellow (labelled 1) which was indicative of a stable composition to reddish brown (labelled 20) which was indicative of a completely degraded composition.

After day 7, the colour of the composition was compared to the colour of the control a freshly prepared composition with deep yellow colour due to the non-degraded retinaldehyde. The colour scores for each composition is shown in the Heat section of Table 6.

UV-Test

Each composition was exposed to UV-radiation according to common UV weathering test conditions (UV range 200 nm to 400 nm) in a UV-chamber by leaving the test sample in a watch glass facing the UV radiation for 48 hours to simulate the effects of sunlight over a prolonged period of time. Retinaldehyde imparts a distinctive yellow colour to the composition. As retinaldehyde photo-degrades, the composition changes colour in a manner of fading/loss of yellow colour. The colour of the composition can therefore be indicative of the degree of degradation of retinaldehyde in the composition. A 20-point colour scale was used to compare the colour of each of the compositions in order to determine the extent of degradation of the composition over time when exposed to UV radiation. The colour scale ranged from deep yellow (labelled 20) which was indicative of a stable composition to off-white (labelled 1) which was indicative of a completely degraded composition. Colour scores were taken using visual analysis of three evaluators, with the final score taken from the average of the three.

After 48 hours, the colour of the composition was compared to the colour of the control a freshly prepared composition with deep yellow colour due to the non-degraded retinaldehyde. The colour scores for each composition is shown in the UV-test section of Table 6.

TABLE 6

| | Heat Test and UV Test | | |
|---|---|---|---|
| | No Stabilisers | Retinaldehyde encapsulated in cyclodextrin without CSO and SPA (A3) | Retinaldehyde encapsulated in cyclodextrin with CSO and SPA (B3) |
| Heat Test | 20 (fully degraded) | 3-4 (stabilised) | 3-4 (stabilised) |
| UV Test | 1 (fully degraded) | 3 (very slightly stabilised) | 17 (stabilised) |

Example 4: —Retinaldehyde with Pure Beta-Carotene—Photo-Degradation

Preparation of Test samples:

A cosmetically acceptable gel composition was prepared through a cold process gelling method by dispersing the thickener in solution and then neutralising by adding a buffering agent as required. A 1% beta-carotene dilution in ethanol (BCD) was used to increase solubility in the gel composition. The beta-carotene was dissolved in ethanol because it has a poor solubility in water-based mediums. The compositions in Table 7 were utilised in the present Example.

Test Protocol:

Each composition was exposed to UV-radiation according to common UV weathering test conditions (UV range 200 nm to 400 nm) in a UV-chamber by leaving the test sample in a watch glass facing the UV radiation for 48 hours to simulate the effects of sunlight over a prolonged period of time. Retinaldehyde imparts a distinctive yellow colour to the composition. As retinaldehyde photo-degrades, the composition changes colour in a manner of fading/loss of yellow colour. The colour of the composition is indicative of the degree of degradation of retinaldehyde in the composition. A 20-point colour scale was used to compare the colour of each of the compositions in order to determine the extent of degradation of the composition over time when exposed to UV radiation. The colour scale ranged from deep yellow (labelled 20) which was indicative of a stable composition to off-white (labelled 1) which was indicative of a completely degraded composition. Colour scores were taken using visual analysis of three evaluators, with the final score being the average of the three.

After 48 hrs, the colour of the composition was compared to the colour of the control a freshly prepared composition with deep yellow colour due to the non-degraded retinaldehyde. The colour score for each composition is shown in Table 8. The concentration of beta-carotene which could be used in this experiment was low due to the fact it imparts a distinct reddish-brown colour to solutions which makes it difficult to observe colour changes at high concentrations. However, as can be observed from the data even at low concentrations there was a synergistic effect between the beta-carotene and the sodium polyaspartate.

TABLE 8

| | UV Test | | |
|---|---|---|---|
| | Composition becomes lighter as it is degraded by UV light | | |
| | Colour Scale: | | |
| | Deep Yellow: 20 (starting colour) | | |
| | Off-white: 1 (fully degraded) | | |
| Samples | Ratios BCD:SPA:RAL | Colour Score at the end point | Synergy of BCD + SPA |
| A4 | 0:0:1 | 1 (fully degraded) | N/A |
| B4 | 0:2:1 | 3 (very slightly stabilised) | N/A |
| C4 | 25:0:1 | 6 (slightly stabilised) | N/A |
| D4 | 25:0.25:1 | 10 | 1 |
| E4 | 20:0.5:1 | 11 (partially stabilised) | 2 |
| F4 | 15:1:1 | 9 | 0 |
| G4 | 5:1.5:1 | 8 | −1 |
| H4 | 2.5:1.75:1 | 8 | −1 |

Example 5: —Retinaldehyde with Carrot Root Extract—Photo-Degradation

Preparation of Test samples:

A cosmetically acceptable emulsion composition was prepared through emulsification by combining oil phase and aqueous phase components. The composition viscosity was adjusted using a thickener. The compositions in Table 9 were utilised in the present Example. The carrot root extract was sourced from Belgium.

Test Protocol:

Each composition was exposed to UV-radiation according to common UV weathering test conditions (UV range 200 nm to 400 nm) in a UV-chamber by leaving the test sample in a watch glass facing the UV radiation for 48 hours to simulate the effects of sunlight over a prolonged period of time. Retinaldehyde imparts a distinctive yellow colour to the composition. As retinaldehyde photo-degrades, the composition changes colour in a manner of fading/loss of yellow colour. The colour of the composition is indicative of the degree of degradation of retinaldehyde in the composition. A 20-point colour scale was used to compare the colour of each of the compositions in order to determine the extent of degradation of the composition over time when exposed to UV radiation. The colour scale ranged from deep yellow (labelled 20) which was indicative of a stable composition to off-white (labelled 1) which was indicative of a completely degraded composition. Colour scores were taken using visual analysis of three evaluators, with the final score being the average of the three.

After 48 hrs, the colour of the composition was compared to the colour of the control a freshly prepared composition with deep yellow colour due to the non-degraded retinaldehyde. The colour score for each composition is shown in Table 10.

The synergy column represents the improvement to stabilising retinaldehyde compositions, relative to the sum of the improvements from individual stabilisers. For example, if the individual colour score of a sample stabilised by carrot root extract alone was 9, and by sodium polyaspartate alone was 2, and the score for a certain combination of the two was 18, the synergy level is +7.

TABLE 10

UV Test:
Composition becomes lighter as it is degraded by UV light
Colour Scale:
Deep Yellow: 20 (starting colour)
Off-white: 1 (fully degraded)

| Samples | Ratios CRE:SPA:RAL | Colour Score at the end point | CRE:SPA Synergy |
|---|---|---|---|
| A5 | 0:0:1 | 1 (fully degraded) | N/A |
| B5 | 0:2:1 | 4 (very slightly stabilised) | N/A |
| C5 | 25:0:1 | 8 (partially stabilised) | N/A |
| D5 | 25:0.25:1 | 14 | 2 |
| E5 | 20:0.5:1 | 15 (stabilised) | 3 |
| F5 | 15:1:1 | 15 (stabilised) | 3 |
| G5 | 5:1.5:1 | 10 | −2 |
| H5 | 2.5:1.75:1 | 9 | −3 |

The invention claimed is:

1. A cosmetic composition comprising:
retinaldehyde; beta-carotene; and
sodium polyaspartate.

2. The cosmetic composition according to claim 1, wherein the beta-carotene is synthetic beta-carotene, isolated beta-carotene, or a plant extract containing beta-carotene.

3. The cosmetic composition according to claim 2, wherein the ratio of synthetic beta carotene or isolated beta carotene to sodium polyaspartate is 1:0.1 to 1:10.

4. The cosmetic composition according to claim 2, wherein the plant extract is from carrot.

5. The cosmetic composition according to claim 4, wherein the carrot extract is at least one of carrot root extract and carrot seed oil extract.

6. The cosmetic composition according to claim 5, wherein the ratio of carrot extract to sodium polyaspartate is 100:1 to 10:1.

7. The cosmetic composition according to claim 6, wherein the ratio of carrot extract to sodium polyaspartate is 40:1 to 15:1.

8. The cosmetic composition according to claim 1, wherein the concentration of retinaldehyde is up to 0.1% weight, wherein the weight percentage is based on total composition weight.

9. The cosmetic composition according to claim 1, wherein the retinaldehyde is cyclodextrin encapsulated.

10. A stabilising composition comprising:
beta-carotene;
sodium polyaspartate; and
retinaldehyde, wherein the beta-carotene and sodium polyaspartate stabilise the retinaldehyde.

11. The stabilising composition according to claim 10, wherein the beta-carotene is synthetic beta-carotene, isolated beta-carotene, or a plant extract containing beta-carotene.

12. A method of stabilising retinaldehyde, the method comprising:
providing a composition comprising beta-carotene, sodium polyaspartate, and retinaldehyde.

13. The method according to claim 12, wherein the beta-carotene is synthetic beta-carotene, isolated beta-carotene, or a plant extract containing beta-carotene.

14. The method according to claim 13, wherein the ratio of synthetic beta carotene or isolated beta carotene to sodium polyaspartate is 1:0.1 to 1:10.

15. The method according to claim 13, wherein the plant extract is from carrot.

16. The method according to claim 15, wherein the carrot extract at least one of carrot root extract and carrot seed oil extract.

17. The method according to claim 16, wherein the ratio of carrot extract to sodium polyaspartate is 100:1 to 10:1.

18. The method according to claim 16, wherein the ratio of carrot extract to sodium polyaspartate is 40:1 to 15:1.

19. The method according to claim 12, wherein the concentration of retinaldehyde is up to 0.1% weight, wherein the weight percentage is based on total composition weight.

* * * * *